United States Patent [19]

Gasteiger et al.

[11] Patent Number: 4,751,312

[45] Date of Patent: Jun. 14, 1988

[54] PROCESS AND INTERMEDIATES FOR THE SYNTHESIS OF DIASTEREOMERIC COMPOUNDS

[75] Inventors: Johann Gasteiger; Karlheinz Kaufmann, both of Munich; Rudolf Mengel, Gau-Algesheim, all of Fed. Rep. of Germany

[73] Assignee: Bayer Aktiengesellschaft, Leverkusen, Fed. Rep. of Germany

[21] Appl. No.: 757,052

[22] Filed: Jul. 19, 1985

[30] Foreign Application Priority Data

Jul. 20, 1984 [DE] Fed. Rep. of Germany ....... 3426906

[51] Int. Cl.$^4$ ................. C07D 249/08; C07D 303/48; C07D 405/04
[52] U.S. Cl. .................................... 548/262; 549/513; 549/550; 549/551; 549/554; 549/563
[58] Field of Search ................ 548/262; 549/550, 513, 549/551, 554, 563

[56] References Cited

U.S. PATENT DOCUMENTS 4,232,033 11/1980 Kramer et al. ...................... 548/262
4,639,462  1/1987 Kramer et al. ...................... 548/262

FOREIGN PATENT DOCUMENTS 2324010 1/1975 Fed. Rep. of Germany ...... 548/262
2102796 2/1983 United Kingdom ................ 548/262
2103210 2/1983 United Kingdom ................ 548/262

OTHER PUBLICATIONS

Tetrahedron Letters, Band 26, Nr. 36, 1985, Seiten 4337–4344, Pergamon Press Ltd., GB; J. Gasteiger et al.: "Nucleophilic Substitution at a Saturated Carbon Atom with Retention of Configuration: The Reaction of Trans-2-halo-3-tert-butyloxiranes with Phenolates".

*Primary Examiner*—Glennon H. Hollrah
*Assistant Examiner*—Patricia L. Morris
*Attorney, Agent, or Firm*—Sprung Horn Kramer & Woods

[57] ABSTRACT

A new process for the controlled synthesis of the two diasteromeric forms of triazolyl-O,N-acetals of the formula

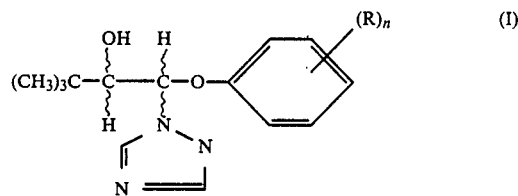

in which
R represents optionally substituted phenyl, optionally substituted phenoxy, optionally substituted alkoxy, optionally substituted alkoxy, optionally substituted alkylthio, alkylcarbonyl, nitro or halogen and
n represents an integer from 0 to 5, with the proviso that R can represent identical or different radicals, if n represents an integer from 2 to 5.

New trans-substituted oxiranes and their use as intermediates for the synthesis of compounds of the formula (I).

8 Claims, No Drawings

PROCESS AND INTERMEDIATES FOR THE SYNTHESIS OF DIASTEREOMERIC COMPOUNDS

The present invention relates to a new process for the controlled synthesis of the two diastereomeric forms of triazolyl-O,N-acetals of the formula

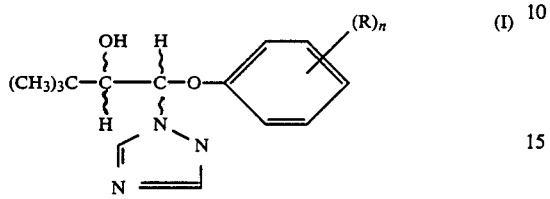

in which

R and n have the meanings given below.

The present invention further relates to new trans-substituted oxiranes and to their use as intermediates for the synthesis of diastereomeric compounds of the formula (I).

It is known that the fungicidally active triazolyl-O,N-acetals of the formula (I) can exist in two different diastereomeric forms (threo and erythro). 1-(4-Chlorophenoxy)-3,3-dimethyl-1-(1,2,4-triazol-1-yl)-butan-2-ol is marketed as a fungicide under the name Triadimenol [DE-OS (German Published Specification) No. 2,324,010].

For biological degradation of triadimefon [1-(4-chlorophenoxy)-3,3-dimethyl-1-(1,2,4-triazol-1-yl)-butan-2-one] [DE-OS (German Published Specification) No. 2,201,063], which is also fungicidally active, a metabolism is proposed in which one of the two diastereomeric forms of triadimenol is predominantly formed, with reduction of the keto group.

It is argued that these metabolites are related to the fungitoxic action of triadimefon [Pestic. Sci 1984 71–77; Zeitschr. f. Pflanzenkr., 1982, 309].

A process for the reduction of triadimefon and compounds of similar structure is known from DE-OS (German Published Specification) No. 2,743,767, in which one of the two diastereomers is predominantly formed. This process has the disadvantage that the main product must first be separated from the by-product by purification processes. In addition, only one of the two diastereomeric forms is thus accessible with an expenditure which is acceptable.

The present invention now provides a new process for the synthesis of the diastereomeric forms (A) and (B) of triazolyl-O,N-acetals of the formula

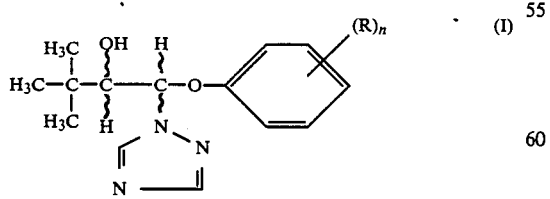

in which

R represents optionally substituted phenyl, optionally substituted phenoxy, optionally substituted alkyl, optionally substituted alkoxy, optionally substituted alkylthio, alkylcarbonyl, nitro or halogen and n represents an integer from 0 to 5, with the proviso that R can represent identical or different radicals if n represents an integer from 2 to 5, in which process an oxirane of the formula

in which

X represents halogen, either (a) is reacted with a phenol of the formula

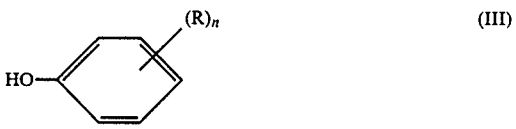

in which

R and n have the above-mentioned meanings, if appropriate in the presence of a base and if appropriate in the presence of a diluent, to give an oxirane derivative of the formula

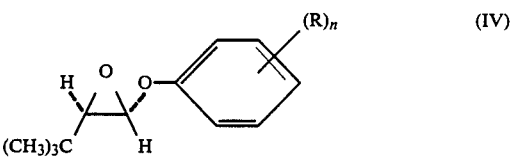

in which

R and n have the above-mentioned meanings, which oxirane derivative, in a second reaction step, is reacted with 1,2,4-triazole or a salt of 1,2,4-triazole, if appropriate in the presence of a diluent, to give a threo-isomer of the formula

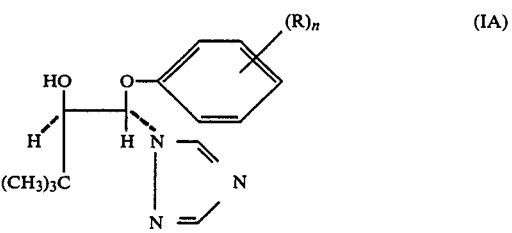

in which

R and n have the above-mentioned meanings, or (b) is reacted with 1,2,4-triazole or a salt of 1,2,4-triazole, if appropriate in the presence of a diluent, to give an oxirane derivative of the formula

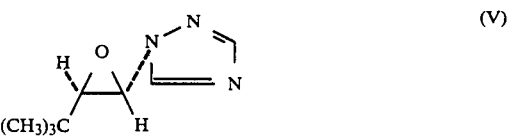

which oxirane derivative, in a second reaction step, is reacted with a phenol of the formula

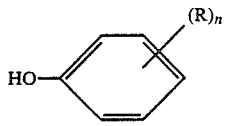 (III)

in which

R and n have the above-mentioned meanings, if appropriate in the presence of a base and if appropriate in the presence of a diluent, to give an erythro-isomer of the formula

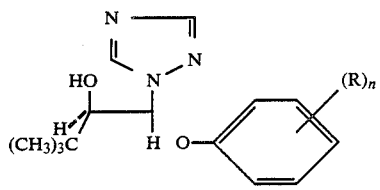 (IB)

in which

R and n have the above-mentioned meanings. Upon carrying out the process according to the invention, trans-3-tert.-butyl-2-halogenooxiranes of the formula

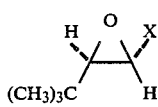 (II-a)

suprisingly react with nucleophiles, such as, for example, sodium phenolates or sodium 1,2,4-triazolide, to give the corresponding trans-substituted oxirane derivatives of the formulae (IV) or (V), the oxirane ring and the configuration on the three-membered ring being retained.

If cis/trans mixtures of oxiranes of the formula (II) are used, the trans-substituted oxirane derivatives of the formula (IV) or (V) are also chiefly formed.

In the subsequent reaction of these oxirane derivatives of the formulae (IV) or (V) with a second nucleophile, the oxirane system of the compounds of the formulae (IV) or (V) reacts with ring-opening, the nucleophile which now enters being bonded to the carbon atom already carrying the first nucleophile.

Because the entry of the second nucleophile furthermore takes place from the side facing away from the oxirane oxygen, the stereochemistry of the resulting product of the formula (I) is unambiguously defined.

Formula (II) provides a definition of the oxiranes required as starting materials in carrying out the process according to the invention. In this formula, X preferably represents chlorine or bromine.

The oxiranes of the formula (II) are known or can be prepared from pinacolone or pivalaldehyde by methods, which are known from the literature. Thus, oxiranes of the formula (II) are obtained by converting pinacolone by halogenation into an α,α-dihalogenoketone of the formula $(CH_3)_3C—CO—CHX_2$ (VI)

in which

X has the above-mentioned meaning, which α,α-dihalogenoketone is then cyclised by the subsequent reduction under alkaline conditions.

Furthermore, oxiranes of the formula (II) can be synthesized by adding a dihalogenocarbenoid onto pivalaldehyde and cyclising the resulting alcohols of the formula $$\begin{array}{c} OH \\ | \\ (CH_3)_3C—CH—CHX_2 \end{array}$$ (VII)

in which

X has the above-mentioned meaning, under basic conditions. This process can be carried out either as a one-stage process or as a two-stage process.

Formula (III) provides a definition of the phenols which are also required as starting materials in carrying out the process according to the invention. In this formula, R preferably represents phenyl optionally substituted by halogen, alkyl with 1 to 4 carbon atoms and/or halogenoalkyl with 1 or 2 carbon atoms and 1 to 5 halogen atoms, or represents phenoxy optionally substituted by halogen, alkyl with 1 to 4 carbon atoms and/or halogenoalkyl with 1 or 2 carbon atoms and 1 to 5 halogen atoms, or represents alkyl with 1 to 4 carbon atoms optionally substituted by halogen, or represents alkoxy with 1 to 4 carbon atoms optionally substituted by halogen, or represents alkylthio optionally substituted by halogen, or represents alkylcarbonyl with 1 to 4 carbon atoms in the alkyl part, nitro, fluorine, chlorine, bromine and iodine. The index n preferably represents an integer from 0 to 3.

Particularly preferred phenols in the process according to the invention are compounds of the formula (III), in which R represents phenyl optionally substituted by fluorine, chlorine, bromine, methyl, ethyl, n-propyl, isopropyl, n-butyl, sec.-butyl, iso-butyl, tert.-butyl, trifluoromethyl, dichlorofluoromethyl and/or difluorochloromethyl, or represents phenoxy optionally substituted by fluorine, chlorine, bromine, methyl, ethyl, n-propyl, isopropyl, n-butyl, sec.-butyl, iso-butyl, tert.-butyl, trifluoromethyl, trichloromethyl, dichlorofluoromethyl and/or difluorochloromethyl, or represents methyl, ethyl, n-propyl, iso-propyl, n-butyl, iso-butyl, sec.-butyl, tert.-butyl, trifluoromethyl, trichloromethyl, dichlorofluoromethyl, difluorochloromethyl, methoxy, ethoxy, trifluoromethoxy, methylthio, ethylthio, trifluoromethylthio, methylcarbonyl, ethylcarbonyl, nitro, fluorine, chlorine and bromine, and n represents 0, 1, 2 or 3.

The compounds listed in the following Table 1 may be mentioned as examples of phenols of the formula (III).

TABLE 1

 (III)

| Rn |
|---|
| 4-Cl |

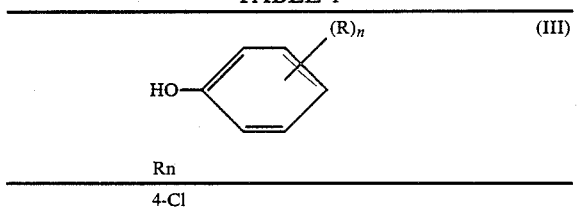

TABLE 1-continued

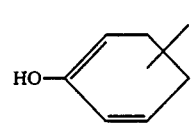

| Rn |
|---|
| 2,4-Cl$_2$ |
| 4-CF$_3$ |
| 4-NO$_2$ |
| 2,4,6-Cl$_3$ |
| 4-F |
| 3-Cl |
| 3,5-Cl$_2$ |
| 2-CH$_3$—CO— |
| 4-CF$_3$O— |
| 4-(4-CF$_3$—⟨⟩—) |
| 4-(4-Cl—⟨⟩—) |
| 4-(2,4-Cl$_2$—⟨⟩—) |
| 4-(4-CH$_3$—⟨⟩—) |
| 4—⟨⟩—O— |

The phenols of the formula (III) are known, or they can be prepared by known methods.

In carrying out variant (a) of the process according to the invention, there are formed oxirane derivatives of the formula (IV) which hitherto have not been described in the literature. Thus the present invention provides as new compounds, oxirane derivatives of the formula

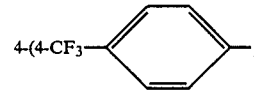

in which
R represents optionally substituted phenyl, optionally substituted phenoxy, optionally substituted alkyl, optionally substituted alkoxy, optionally substituted alkylthio, alkylcarbonyl, nitro or halogen and
n represents an integer from 0 to 5,
with the proviso that R can represent identical or different radicals, if n represents an integer from 2 to 5.

In this formula (IV), R and n preferably have those meanings which have already been mentioned as preferred meanings for this radical and for this index in connection with the description of the phenols of the formula (III).

The compounds listed in the following Table 2 may be mentioned as examples of oxirane derivatives of the formula (IV).

TABLE 2

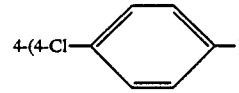

| Rn | Rn |
|---|---|
| 4-Cl | 2-CH$_3$—CO— |
|  | 4-CF$_3$O— |
| 4—⟨⟩— |  |
| 2,4-Cl$_2$ |  |
|  | 4-(4-CF$_3$—⟨⟩—) |
| 4-CF$_3$ |  |
|  | 4-(4-Cll—⟨⟩—) |
| 4-NO$_2$ |  |
|  | 4-(2,4-Cl$_2$—⟨⟩—) |
| 2,4,6-Cl$_3$ |  |
|  | 4-(4-CH$_3$—⟨⟩—) |
| 4-F |  |
|  | 4—⟨⟩—O— |
| 3-Cl |  |
| 3,5-Cl$_2$ |  |

In carrying out variant (b) of the process according to the invention, there is formed the oxirane-derivative of the formula (V) which hitherto has also not been described in the literature. Thus, the present invention also provides, as a new compound, the oxirane derivative of the formula

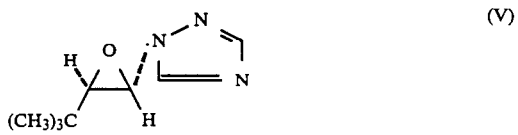

The formula (IA) and (IB) provide a definition of the diastereomeric forms (A) and (B) which can be prepared by the process according to the invention. In these formulae, R and n preferably have those meanings which have already been mentioned as preferred meanings for the radical R and for the index n in connection with the description of the phenols of the formula (III).

The compounds listed in the following Table 3 may be mentioned as examples of diastereomers of the formula (IA) and (IB).

TABLE 3

(IA) threo structure with HO, H, (CH$_3$)$_3$C, H, N, triazole, (R)$_n$ on phenyl via O and (IB) erythro structure with HO, H, (CH$_3$)$_3$C, H, triazole-N, O-phenyl-(R)$_n$

| Rn |
|---|
| 4-Cl |
| 4-(phenyl) |
| 2,4-Cl$_2$ |
| 4-CF$_3$ |
| 4-NO$_2$ |
| 2,4,6-Cl$_3$ |
| 4-F |
| 3-Cl |
| 3,5-Cl$_2$ |
| 2-CH$_3$—CO— |
| 4-CF$_3$O— |
| 4-(4-CF$_3$—phenyl—) |
| 4-(4-Cl—phenyl—) |
| 4-(2,4-Cl$_2$—phenyl—) |
| 4-(4-CH$_3$—phenyl—) |
| 4-(phenyl—O—) |

In carrying out variant (a) of the process according to the invention, the phenols of the formula (III) are either used in the presence of bases or in the form of phenolates. Bases which can preferably be used are alkali metal hydroxides, such as sodium hydroxide or potassium hydroxide, furthermore hydrides, such as sodium hydride, and also alcoholates, such as potassium tert.-butylate. Preferred phenolates are alkali metal phenolates, such as sodium or potassium phenolate.

Possible diluents in carrying out the first stage of variant (a) of the process according to the invention are all inert organic solvents usually suitable for such reactions. Preferred diluents are nitriles, such as acetonitrile, furthermore aromatic hydrocarbons, such as benzene, toluene and xylene, and also ethers, such as diethylether and tetrahydrofuran, as well as polar aprotic solvents, such as dimethylformamide and dimethylsulphoxide.

In carrying out variant (a) of the process according to the invention, the triazole is used in the second stage either in the presence of bases, such as potassium or sodium hydroxide, or in the form of the sodium or potassium salt of triazole.

In carrying out the second stage of variant (a) of the process according to the invention, preferred diluents are alcohols, such as methanol or ethanol.

The reaction temperatures can be varied within a substantial range in carrying out variant (a) of the process according to the invention. In the first stage, the reaction is generally carried out at temperatures between −10° C. and +100° C., preferably between 0° C. and 50° C. In the second stage, the reaction is generally carried out at temperatures between 50° and 120° C., preferably between 60° and 100° C.

In carrying out variant (b) of the process according to the invention, the triazole is either used in the presence of bases, such as potassium or sodium hydroxide, or is used in the form of the sodium or potassium salt of triazole.

Possible diluents in carrying out the first stage of variant (b) of the process according to the invention are all inert organic solvents usually suitable for such reactions.

Preferred solvents which can be used are all those solvents which have already been mentioned as preferred solvents in connection with the first stage of variant (a) of the process according to the invention.

In carrying out variant (b) of the process according to the invention, the phenols of the formula (III) are used in the second stage either in the presence of bases or in the form of phenolates. Preferred are those bases or phenolates which have already been mentioned as preferred in connection with variant (a).

In carrying out the second stage of variant (b) of the process according to the invention, preferred diluents are again alcohols, such as methanol or ethanol.

The reaction temperatures can also be varied within a substantial range in carrying out variant (b) of the process according to the invention. In the first stage, the reaction is generally carried out at temperatures between 0° C. and 60° C., preferably between 10° C. and 50° C. In the second stage, the reaction is generally carried out at temperatures between 50° and 120° C., preferably between 60° and 100° C.

In carrying out variants (a) and (b) of the process according to the invention, working up and isolation of the reaction products is effected by customary methods.

The compounds which can be prepared by the process according to the invention exhibit very good fungicidal properties.

The process according to the invention is illustrated by the following examples.

Preparation of the starting compounds starting from pinacolone:

EXAMPLE 1

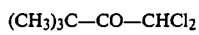 (VI-1)

Chlorine was passed into a mixture of 40 g of pinacolone and 10 ml water at 0° C. to saturation. The dichloro compound thereby formed crystallised out spontaneously and was recrystallised from petroleum ether (60°–90°).

Yield: 27.2 g (45%) of 1,1-dichloro-3,3-dimethylbutan-2-one as colourless needles of melting point 51° C.

EXAMPLE 2

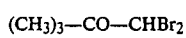 (VI-2)

35.00 g of bromine were added dropwise to a mixture of 100 g of pinacolone with 300 ml of diethyl ether and 180 ml of dioxane at 35°–40° C., with stirring. Towards the end of the reaction, the solution became coloured. It was shaken with NaHSO$_3$/water until the bromine colour disappeared, washed with water and concentrated in a rotary evaporator. The pale orange product thereby obtained was recrystallised from n-hexane.

Yield: 206 g (81%) of 1,1-dibromo-3,3-dimethylbutan-2-one of melting point 75° C.

EXAMPLE 3

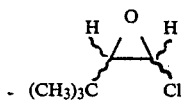 (II-1)

A solution of 67.6 g of 1,1-dichloro-3,3-dimethylbutan-2-one in 160 ml of diethyl ether was added dropwise to a solution of 28.0 g of sodium hydroxide in 120 ml of water and 50 ml of methanol. 10 g of NaBH$_4$ were introduced in portions, while cooling to −10° C. and stirring. When the reaction had subsided, stirring was continued at room temperature for a further 24 hours. The organic phase was separated off, the aqueous phase was extracted twice by shaking with ether and the combined organic phases were dried and carefully concentrated at 30° C. in vacuo over a 1 m long Vigreux column.

The crude solution of the oxirane in ether was 82% strength and contained a maximum of 1% of impurities.

Yield: 62.9 g of solution=51.6 g of 3-tert.-butyl-2-chloroxirane (96%).

A main fraction was isolated by distillation of the ethereal solution.

Yield: 48.7 g (90%) of 3-tert.-butyl-2-chloroxirane as a colourless liquid of boiling point$_{13}$=31° C.

The cis:trans isomer ratio was determined by NMR spectroscopy: cis:trans=12:88.

EXAMPLE 4

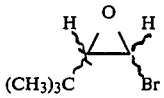 (II-2)

2-Bromo-3-tert.-butyl-oxirane was obtained as the product from 51.6 g of 1,1 dibromo-3,3-dimethyl-butan-2-one according to the method described in Example 3.

Yield: 25.8 g (72%) of 2-bromo-3-tert.-butyl-oxirane as a 1:9 mixture of cis/trans isomers.

Preparation of starting compounds starting from pivalaldehyde:

EXAMPLE 5

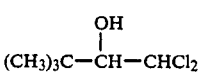 (VII-1)

0.20 mol of butyl-lithium (1.6N in hexane) were added dropwise to a mixture of 17.00 g of methylene chloride in 300 ml of tetrahydrofuran, ether and hexane (4:1:1) at −80° C. The mixture was subsequently stirred at the same temperature for 30 minutes and a solution of 17.2 g of pivalaldehyde in 100 ml of ether was then added dropwise. The reaction mixture was left in a Dewar vessel for 12 hours, where it warmed slowly. It was then concentrated in a rotary evaporator and the viscous residue was taken up in 50 ml each of ether and water. The aqueous phase was extracted twice more with ether, the combined phases were dried over Na$_2$SO$_4$, the solvent was distilled off and the residue was then recrystallised from pentane.

Yield: 20.6 g (67%) of 1,1-dichloro-3,3-dimethylbutan-2-ol as colourless needles of melting point 49° C.

EXAMPLE 6

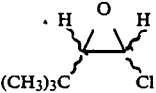 (II-1)

37.0 ml of 3N aqueous sodium hydroxide solution were added dropwise to 17.10 g of 1,1-dichloro-3,3-dimethylbutan-2-ol at 0° C., with vigorous stirring. After 1 hour, the ice-cooling was removed and stirring was continued at room temperature for a further 14 hours. The organic phase was then separated off, washed with water, dried over a molecular sieve (4 Å) and distilled under a waterpump vacuum.

Yield: 11.4 g (85%) of 2-chloro-3-tert.-butyloxirane as a liquid of boiling point$_{13}$:35° C. The cis/trans isomer ratio was cis:trans=12:88.

EXAMPLE 7

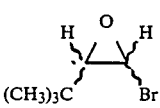 (II-2)

0.20 mol of butyl-lithium (1.6N in hexane) were added dropwise to 22.4 g of diisopropylamine in 400 ml of tetrahydrofuran, 100 ml of diethyl ether and 100 ml of hexane at −10° C. and the solution was left to react at room temperature for 1 hour.

It was then cooled to −80° C. and a solution of 17.00 g of dibromomethane in 40 ml of diethyl ether was added dropwise in the course of 45 minutes. After a further 30 minutes, 17.2 g of pivalaldehyde, dissolved in 70 ml of diethyl ether, were carefully added dropwise in the course of 1 hour. The mixture was subsequently stirred for 15 hours, during which the reaction solution slowly warmed to room temperature. After the solution had been concentrated in a rotary evaporator, the suspension was taken up in 50 ml each of water and diethyl ether, the organic phase was washed with water, dried over $Na_2SO_4$ and concentrated in a rotary evaporator and the residue was distilled under a waterpump vacuum.

Yield: 17.55 g (49%) of 2-bromo-3-tert.-butyloxirane as a liquid of boiling point$_{11}$=42° C.

The cis:trans isomer ratio was determined by NMR spectroscopy: cis/trans=1.5/98.5.

EXAMPLE 8

Synthesis of the two diastereomeric forms of 1-(4-chlorophenoxy)-3,3-dimethyl-1-(1,2,4-triazol-1-yl)-butan-2-ol (a) trans-2-tert.-Butyl-3-(4-chlorophenoxy)-oxirane

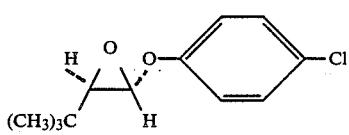
(IV-1)

9.75 g of sodium p-chlorophenolate, suspended in 15 ml of acetonitrile, were added to 10.0 g of a cis/trans isomer mixture of 2-bromo-3-tert.-butyloxirane (cis/tans=1/9) in 5 ml of acetonitrile, while cooling with ice. The solution was stirred at room temperature for a further 50 hours. During this, the solution became slightly brownish in colour and a white precipitate formed. The suspension was concentrated and the residue was taken up in 20 ml each of diethyl ether and water. The organic phase was washed with 3N aqueous sodium hydroxide solution and water, dried over $Na_2SO_4$ and concentrated and the residue was distilled under a high vacuum.

Yield: 8.85 g (71%) of trans-2-tert.-butyl-3-(4-chlorophenoxy)oxirane of boiling point$_{0.01}$:55° C.

(b) trans-3-tert-Butyl-2-(1,2,4-triazol-1-yl)-oxirane

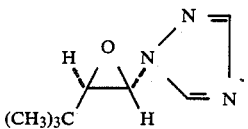
(V-1)

10.62 g (59 mmol) of 2-bromo-3-tert.-butyloxirane (cis:trans=1.5:98.5) and 1.50 g of 15-crown-5 were added to a suspension of 5.92 g (65 mmol) of sodium 1,2,4-triazole in 70 ml of acetonitrile at room temperature. The suspension was stirred at 30° C. for 140 hours and the solvent was then removed on a rotary evaporator, the residue was taken up in ether and the mixture was washed twice with water, dried over $Na_2SO_4$ and concentrated. The pale yellowish crude product (5.0 g; 50%) was purified by distillation under a high vacuum.

Yield: 3.85 g (39%) of trans-3-tert.-butyl-2-(1,2,4-triazol-1-yl)oxirane as a colourless liquid of boiling point: 34° C. under $6\times10^{-3}$ mbar.

(c) threo-1-(4-Chlorophenoxy)-3,3-dimethyl-1-(1,2,4-triazol-1-yl)-butan-2-ol

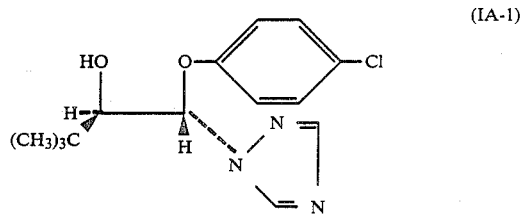
(IA-1)

1.13 g of trans-2-tert.-butyl-(4-chlorophenoxy)oxirane were dissolved in 10 ml of methanol, together with 0.68 g of sodium triazolide, and the solution was stirred under reflux for 22 hours. The solvent was then distilled off, the residue was taken up in 25 ml each of methylene chloride and water, the organic phase was separated off, rinsed with water, dried over $Na_2SO_4$ and concentrated again and the residue was separated on silica gel with petroleum ether/ethyl acetate (2:8).

Yield: 0.89 g (60%) of threo-1-(chlorophenoxy)-3,3-dimethyl-1-(1,2,4-triazol-1-yl)-butan-2-ol as colourless crystals of melting point 138°–139° C., and as by-products, 0.09 g (6%) of threo-1-(4-chlorophenoxy)-3,3-dimethyl-1-(1,2,4-triazol-2-yl)-butan-2-ol of melting point 216°–218° C. and 0.08 g (9.6%) of 3,3-dimethyl-2-(1,2,4-triazol-1-yl)butanal as a pale yellowish liquid.

(d) erythro-1-(4-Chlorophenoxy)-3,3-dimethyl-1-(1,2,4-triazol-1-yl)-butan-2-ol

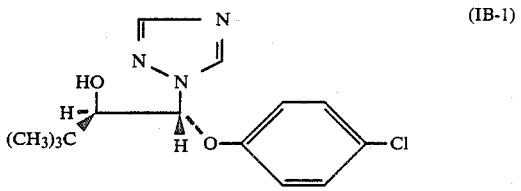
(IB-1)

0.84 g of trans-2-tert.-butyl-3-(1,2,4-triazol-1-yl)-oxirane were heated under reflux with 2.25 g of sodium p-chlorophenolate in 10 ml of methanol for 120 hours. The solvent was removed, the residue was taken up in ethyl acetate and the mixture was washed with 3N aqueous NaOH and water. The organic phase was dried with $Na_2SO_4$ and concentrated and the residue was chromatographed on silica gel with petroleum ether/ethyl acetate (2:8)

Yield: 0.25 g (17%) of erythro-1-(4-chlorophenoxy)-3,3-dimethyl-1-(1,2,4-triazol-1-yl)-butan-2-ol as colourless crystals of melting point 132° C.

It will be understood that the specification and examples are illustrative but not limitative of the present invention and that other embodiments within the spirit and scope of the invention will suggest themselves to those skilled in the art.

What is claimed is:

1. A process for the synthesis of the diastereomeric forms (A) and (B) of triazolyl-O,N-acetals of the formula

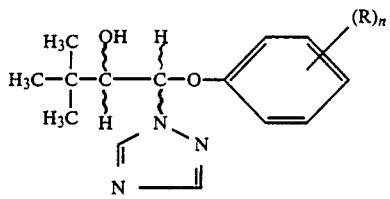 (I)

in which
R represents phenyl optionally substituted by halogen, alkyl with 1 to 4 carbon atoms and/or halogenalkyl with 1 or 2 carbon atoms and 1 to 5 halogen atoms, or represents phenoxy optionally substituted by halogen, alkyl with 1 to 4 carbon atoms and/or halogenoalkyl with 1 or 2 carbon atoms and 1 to 5 halogen atoms, or represents alkyl with 1 to 4 carbon atoms optionally substituted by halogen, or represents alkoxy with 1 to 4 carbon atoms optionally substituted by halogen, or represents alkylthio with 1 to 4 carbon atoms and optionally substituted by halogen, or represents alkylcarbonyl with 1 to 4 carbon atoms in the alkyl part, nitro, fluorine, chlorine, bromine and iodine, and
n represents an integer from 0 to 5, with the proviso that
R can represent identical or different radicals, if n. represents an integer from 2 to 5, which process comprises reacting an oxirane of the formula

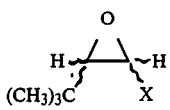 (II)

in which
X represents halogen,
either
(a) with a phenol of the formula

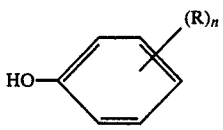 (III)

in which
R and n have the above-mentioned meanings,
if appropriate in the presence of a base and if appropriate in the presence of a diluent, to give an oxirane derivative of the formula

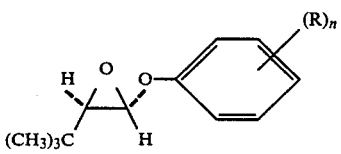 (IV)

in which
R and n have the above-mentioned meanings,
which oxirane derivative, in a second reaction step, is reacted with 1,2,4-triazole or a salt of 1,2,4-triazole, if appropriate in the presence of a diluent, to give a threo-isomer of the formula

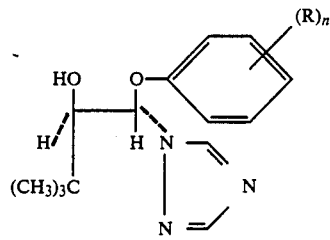 (IA)

in which
R and n have the above-mentioned meanings, or
(b) with 1,2,4-triazole or a salt of 1,2,4-triazole, if appropriate in the presence of a diluent, to given an oxirane derivative of the formula

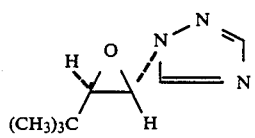 (V)

which oxirane derivative, in a second reaction step, is reacted with a phenol of the formula

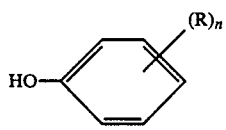 (III)

in which
R and n have the above-mentioned meanings, if appropriate in the presence of a base and if appropriate in the presence of a diluent, to give an erythro-isomer of the formula

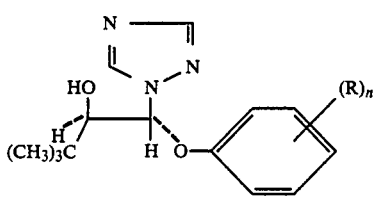 (IB)

in which
R and n have the above-mentioned meanings.

2. A process as claimed in claim 1, wherein the oxirane is a compound of the formula (II), in which X is chlorine or bromine.

3. A process as claimed in claim 1, wherein the phenol is a compound of the formula (III), in which n is an integer from 0 to 3.

4. A process as claimed in claim 1, wherein the starting material of the formula (III) is 4-chloro-phenol.

5. A process as claimed in claim 1, wherein the starting material of the formula (III) is 4-phenyl-phenol.

6. A process as claimed in claim 1, which comprises reacting 2-bromo-3-tert.-butyl-oxirane of the formula

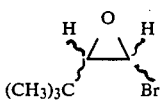 (II-2)

with 4-chloro-phenol of the formula

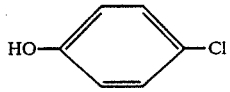
(III-1)

in the form of the sodium salt in the presence of acetonitrile, to give the oxirane derivative of the formula

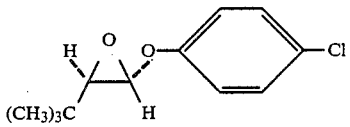
(IV-1)

which oxirane derivative, in a second reaction step, is reacted with 1,2,4-triazole in the form of the sodium salt in the presence of methanol, to give the threo-1-(4-chloro-phenoxy)-3,3-dimethyl-1-(1,2,4-triazol-1-yl)-butan-2-ol of the formula

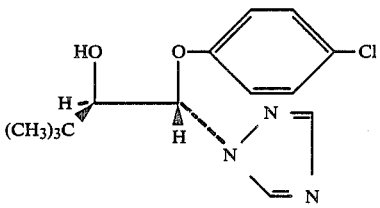
(IA-1)

7. A process as claimed in claim 1, which comprises reacting 2-bromo-3-tert.-butyl-oxirane of the formula

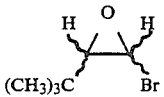
(II-2)

with 4-phenyl-phenol of the formula

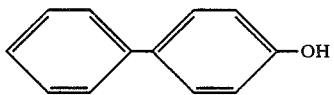
(III-2)

in the form of the sodium salt in the presence of acetonitrile, to give the oxirane derivative of the formula

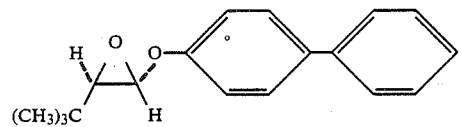
(IV-2)

which oxirane derivative, in a second reaction step, is reacted with 1,2,4-triazole in the form of the sodium salt in the presence of methanol, to give the threo-1-(4-phenyl-phenoxy)-3,3-dimethyl-1-(1,2,4-triazol-1-yl)-butan-2-ol of the formula

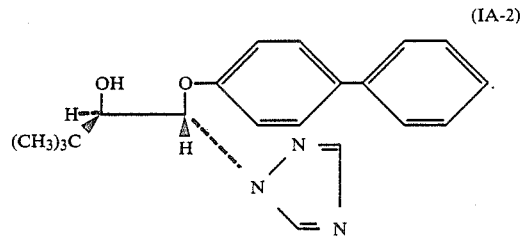
(IA-2)

8. A process as claimed in claim 1, which comprises reacting 2-bromo-3-tert.-butyl-oxirane of the formula

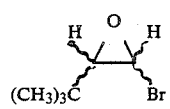
(II-2)

with 1,2,4-triazole in the form of the sodium salt in the presence of acetonitrile, to give the oxirane derivative of the formula

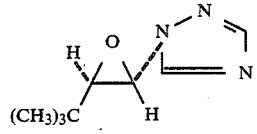
(V)

which oxirane derivative, in a second reaction step, is reacted with 4-chloro-phenol of the formula

(III-1)

in the form of the sodium salt in the presence of methanol, to give the erythro-1-(4-chloro-phenoxy)-3,3-dimethyl-1-(1,2,4-triazol-1-yl)-butan-2-ol of the formula

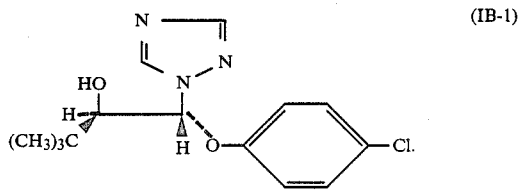
(IB-1)

* * * * *